United States Patent
McAuley et al.

(10) Patent No.: US 8,636,002 B2
(45) Date of Patent: Jan. 28, 2014

(54) HUMIDIFIER WITH INTERNAL HEATING ELEMENT AND HEATER PLATE

(75) Inventors: Alastair Edwin McAuley, Auckland (NZ); Raymond Ka Yau Lo, Auckland (NZ); David Fraser Wixey, Auckland (NZ); Ian Douglas Makinson, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 1011 days.

(21) Appl. No.: 12/438,606

(22) PCT Filed: Aug. 24, 2007

(86) PCT No.: PCT/NZ2007/000228
§ 371 (c)(1),
(2), (4) Date: Oct. 16, 2009

(87) PCT Pub. No.: WO2008/024001
PCT Pub. Date: Feb. 28, 2008

(65) Prior Publication Data
US 2010/0043791 A1 Feb. 25, 2010

(30) Foreign Application Priority Data
Aug. 25, 2006 (NZ) ........................................ 549483

(51) Int. Cl.
*F23D 11/00* (2006.01)
*F23D 14/00* (2006.01)

(52) U.S. Cl.
USPC ............ 128/203.26; 128/203.14; 128/203.27; 128/203.12; 128/204.14; 128/204.17; 128/204.18; 261/142; 261/156

(58) Field of Classification Search
USPC ............. 128/203.26, 203.14, 203.27, 203.12, 128/203.15, 203.16, 203.17, 204.14, 128/204.17, 204.18; 261/142, DIG. 65, 261/119.1, DIG. 46, 130, 129, 153, 156; 239/135, 136; 122/4 R, 31.1
See application file for complete search history.

(56) References Cited

U.S. PATENT DOCUMENTS

| 4,272,014 A | * | 6/1981 | Halfpenny et al. ......... 236/44 B |
| 4,753,758 A | | 6/1988 | Miller |
| 4,955,372 A | * | 9/1990 | Blackmer et al. ........ 128/203.16 |
| 6,918,389 B2 | | 7/2005 | Seakins et al. |
| 2001/0049465 A1 | * | 12/2001 | Goldberg et al. ............... 600/22 |

FOREIGN PATENT DOCUMENTS

| GB | 2 192 136 | 1/1988 |
| GB | 2 293 325 | 3/1996 |
| WO | 01/02043 | 1/2001 |

* cited by examiner

*Primary Examiner* — Justine Yu
*Assistant Examiner* — Colin W Stuart
(74) *Attorney, Agent, or Firm* — Knobbe, Martens, Olson & Bear, LLP

(57) ABSTRACT

A respiratory humidifier chamber for use with a breathing assistance apparatus is described. The chamber includes a water-tight vessel having an inlet for receiving gases from the breathing assistance apparatus, and an outlet through which heated humidified gases exit the vessel for delivery to a patient. The chamber has a partition which divides the chamber into upstream and downstream sub-chambers. The sub-chambers are separated by the partition except for an aperture which passes through the partition and allows gaseous communication between the sub-chambers. The downstream sub-chamber includes a heater base which heats a volume of water contained within it. The aperture is located above the volume of water. The upstream sub-chamber contains an internal heater which heats gases passing through it from the inlet to the aperture. At least part of the internal heater is located immediately adjacent the aperture.

29 Claims, 11 Drawing Sheets

HUMIDIFIER WITH INTERNAL HEATING ELEMENT AND HEATER PLATE

This application is a National Phase filing of PCT/NZ2007/000228, having an International filing date of Aug. 24, 2006, which disclosure is herein incorporated by reference.

BACKGROUND OF THE INVENTION

1. Field of the Invention

This invention relates to a gases supply and gases humidification apparatus, particularly, but not solely, for providing respiratory assistance to patients or users who require a supply of gas at positive pressure for the treatment of diseases such as Obstructive Sleep Apnea (OSA), snoring or Chronic Obstructive Pulmonary Disease (COPD) and the like. In particular, this invention relates to a humidifier chamber for use in a gases supply apparatus.

2. Summary of the Prior Art

A number of methods are known in the art for supplying humidified gases to a patient to assist a patient's breathing. Continuous Positive Airway Pressure (CPAP) involves the administration of air under pressure to a patient, usually by passing gases to the patient or user through a nasal mask. CPAP therapy is used in the treatment of snoring and Obstructive Sleep Apnoea (OSA), a condition characterised by repetitive collapse of the upper airway during inspiration. Positive pressure splints the upper airway open, preventing collapse. Treatment of OSA with CPAP has proven generally to be both effective and safe.

CPAP is also commonly used for patients with a variety of respiratory illnesses, including COPD (Chronic Obstructive Pulmonary Disease).

One of the side effects of CPAP therapy is that the stream of air can dry the nasal membranes, or the mouth and throat membranes of a user. This can lead to these areas becoming inflamed and uncomfortable. In order to counteract this side effect, it is usual for the air that is provided to a user to be humidified, by adding a humidification chamber or similar into the gases stream before the gas is provided to the patient. The gases enter the humidifier chamber, and are humidified as they pass over a volume of heated water contained in the chamber.

An ideal system is one that can deliver gas at the required pressure and temperature, with a maximum amount or maximum volume of water vapour contained in the gas. That is, gas at substantially 100% saturation or absolute humidity, delivered to a user at a relatively high temperature (the higher the temperature of the gas, the greater the volume of water vapour that it can contain). An ideal delivery temperature is one that is either the same as or slightly higher than the body temperature of the user.

Although systems exist that locate the humidifier close to the user, this arrangement tends to add weight close to the patient, and can increase their discomfort and decrease the usability of the system. Therefore, it is usual to locate the humidifier chamber remotely from the patient, with the heated humidified gases transported to the patient via a heated conduit.

A known (prior art) example of a system where the humidifier chamber is located remotely from the user is shown in FIG. 1. Gases are passed to the patient by way of a patient interface 2. In the system shown in FIG. 1, the interface 2 is a nasal cannula. However, full-face masks, nasal masks, nasal cannulas, oral mouthpieces, tracheostomy connections, or any other suitable interface can be used with these systems.

The cannula 2 is connected to a gases transportation pathway or inspiratory conduit 3 that in turn is connected to a humidifier chamber 5. A flow of gases is provided through the chamber 5 by an integrated blower unit contained within the housing 10.

Atmospheric air enters the housing 10 through an inlet 9 on the back of the casing 10, and is pressurised by a blower or fan assembly. The air is then passed into the humidification chamber 5 through an inlet 11. The humidification chamber 5 extends out from the housing 10 and can be removed and replaced by the patient or other user. The chamber 5 contains a volume of water that is heated via the base 13 of the chamber 5. The base 13 is heated by contact with an adjacent heated plate (not shown) that forms part of the system contained within the casing 10. The inspiratory conduit 3 is connected to the outlet 8 of the humidification chamber 5. It is usual for the walls of inspiratory conduit 3 to contain heating means or heater wires 7 that heat the walls of the conduit to reduce or eliminate the formation of condensation.

The gases supply and humidifying device contained within the housing 10 can be provided with a control means or an electronic controller such as a microprocessor that executes computer software commands stored in an associated memory. The user of the device may set a predetermined required value (preset value) of humidity or temperature of the gases supplied to patient 1, via a control interface such as a dial or buttons on a control pad or panel.

In response to the user set humidity or temperature value input, and other possible inputs such as system sensors that sense gases flow or temperature, the controller determines when (or to what level) to energise the heater plate. This in turn heats the volume of water 6 within humidification chamber 5 (via the conductive base 13). Water vapour fills the volume of the chamber above the surface of the water 6, rising from the surface of the water 6. Gases from the blower or fan pass into the chamber 5 through inlet 11 and become humidified as they pass across the top half of the chamber 5, that is, that part of the chamber 5 not filled with water 6.

The heated and humidified gas then passes out of the humidification chamber 5 via outlet 8 as fresh gases from the blower enter the chamber and displace the humidified, saturated gases.

The supply of gases through the inlet 11 is varied by a variable speed pump or fan 19 that draws air or other gases through the inlet 9. The speed of the variable speed pump or fan is preferably controlled by the control means or electronic controller described above.

Typically, humidification chambers such as chamber 5 are formed as a hollow shell with an open base. The shell is typically formed from a plastics material. A highly heat conductive metal plate 13 is added to close the open base, closing and sealing the chamber 5, except for the inlet 11 and outlet 8. In use, the base 13 is in direct contact with the heater plate. When the chamber 5 is in position substantially the entire surface area of the base 13 contacts the heater plate.

It should be noted that FIG. 1 merely illustrates one form of a suitable integrated gases supply and humidifying device. Other suitable gases supply systems, for example those that use fully separate or independent blowers and humidifiers connected in series, can also be used.

There are several disadvantages when using prior art systems of the type described above where the humidification chamber is located remotely from the patient. Some of these disadvantages are outlined below:

It is normally assumed that gases leaving the humidifier chamber are in a state of absolute humidity (100% saturated with water vapour). As described above, this saturated condition is desirable as it delivers a maximum amount of water vapour to the end user, and minimises any drying out of nasal or throat membranes. However, there is no guarantee that the gases leaving such humidifiers are in fact 100% saturated. This is because the saturation state of the gas leaving the chamber depends on a number of factors, including the temperature of the gas as it enters the chamber, the temperature of the water in the chamber, and the rate at which the gas passes through the chamber. Typically, humidification systems are only controlled to achieve a desired outlet gas temperature (not humidity).

Intermittent or varying flow rates (caused for example by fluctuating demand from the user's breathing) will cause the humidity of the gas passing out from the humidity chamber to be uneven. Air that passes through the humidifier at a high flow rate has had little time to be heated and humidified, while low flow rate gas lingers in the chamber longer, and therefore absorbs more water vapour, leaving the chamber at a higher absolute humidity. Varying flow rates caused by fluctuating user demand cause the flow rate of the gas through the chamber to vary at a greater rate than it is possible to compensate for using a control/feedback loop. It is not possible to compensate for varying flow rates by varying the inputs, e.g. varying heater power.

It is usual for humidifiers of the prior art type to be heated from the base. That is, the base of the humidifier chamber is made of a conducting material, with the volume of water in the chamber heated via this base. Air from the respirator or blower enters the chamber at or towards one side, above the level of the water within the chamber. The air passes over the heated water and becomes humidified, and then exits the chamber at the far side. This arrangement can be inefficient If air or gas enters the chamber at a lower temperature than the water and the saturated vapour in the chamber, it is likely that the gas will exit the chamber in a state where it is not fully saturated (not in a state of absolute humidity).

In an attempt to overcome or minimise these difficulties, some prior art systems preheat gases before they enter the humidification chamber. However, these gases can lose heat energy as they travel from the pre-heater to the humidification chamber. It is usually not possible to retrofit a pre-heater in an existing blower unit. Therefore, in a gases supply and gases humidification system if a pre-heater is to be added, the blower unit most often needs to be replaced. This can be expensive.

U.S. Pat. No. 6,918,389 discloses a humidifier and sensor for use with a breathing assistance apparatus. A number of different configurations of humidification chambers are disclosed. Also disclosed are a number of methods and apparatus for heating the gases passing through the humidifier chambers. In particular, this patent discloses chambers that include an internal heating element such as a metal scroll element, a porous material element, or a semipermeable membrane. These elements provide both wet and dry heating of the gases passing through the chamber. This patent also discloses using heaters to preheat gases entering the chamber.

U.S. Pat. No. 4,753,758 discloses a respiratory humidifier with an internal partition wall, dividing the humidifier into a water reservoir and a humidification enclosure. The partition wall allows water vapour or humidified gas to pass through from the water reservoir to the humidification enclosure, but does not allow liquid water or water in droplet form to pass through. A second heater, having the form of a conical finned heater, can be located in the humidification enclosure to provide additional heating. The finned heater as described is centrally located and there is no direct heating of the gases passing through the inlet or outlet ports of the humidifier. The partition wall described includes a filter element. Several different alternative filter constructions are described. A certain amount of system pressure is required to force the water and gas through filters of this type.

DISCLOSURE OF THE INVENTION

It is an object of the present invention to provide a breathing assistance apparatus which goes some way to overcoming the abovementioned disadvantages or which at least provides the public or industry with a useful choice.

Accordingly in a first aspect the present invention consists in a respiratory humidifier chamber for use with a breathing assistance apparatus, said chamber comprising:

a watertight vessel having an inlet adapted for receiving gases from said breathing assistance apparatus, and an outlet through which heated humidified gases exit said vessel for delivery to a patient, a partition, dividing said vessel into an upstream sub-chamber and a downstream sub-chamber, said sub-chambers sealed from each other by said partition except for an aperture, said aperture passing through said partition and allowing gaseous communication between said sub-chambers, said downstream sub-chamber including a heater base, adapted to heat a volume of water contained within said downstream sub-chamber in use, said aperture located above said volume of water in use, said upstream sub-chamber containing an internal heater, adapted to heat gases passing through said upstream sub-chamber from said inlet to said aperture, at least part of said internal heater located immediately adjacent said aperture.

Preferably said internal heater is configured so as to provide a tortuous path for said gases as they pass through said upstream sub-chamber.

Preferably said internal heater is a fin heater having a plurality of fins.

Preferably the fins of said fin heater are aligned substantially perpendicular to a direct flow path between said inlet and said aperture.

Preferably said tortuous path is formed by offsetting adjacent ones of said fins.

Preferably said heater base and said internal heater are separate.

Alternatively said heater base and said internal heater are a single heater, controlled and powered from a single source.

In a second aspect the present invention consists in a breathing assistance apparatus for delivery of respiratory gases to a patient comprising.

a gases supply device, adapted to provide a flow of pressurised gases through said system, a humidifier chamber, having an inlet and an outlet, said chamber adapted to receive said flow of gases from said breathing assistance apparatus via said inlet, and provide a supply of heated humidified gases through said outlet, a delivery conduit, adapted to connect to said outlet and receive said heated humidified gases, a patient delivery interface, adapted to receive said gases from said delivery conduit and deliver these to said patient, said humidifier chamber comprising a watertight vessel having an inlet adapted for receiving gases from said breathing assistance apparatus, and an outlet for delivering heated humidified gases to a patient via said conduit and said interface, a partition, dividing said vessel into an upstream sub-chamber and a downstream sub-chamber, said sub-chambers sealed from each other except for an aperture passing through said partition, said aperture allowing gaseous communication between said sub-chambers, said downstream sub-chamber including a heater base, adapted to heat a volume of water contained within said downstream sub-chamber in use, said aperture located above said volume of water in use, said upstream sub-chamber containing an internal heater, adapted to heat gases passing through said upstream sub-chamber from said inlet to said aperture, at least part of said internal heater located immediately adjacent said aperture.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

The invention consists in the foregoing and also envisages constructions of which the following gives examples.

BRIEF DESCRIPTION OF THE DRAWINGS

Preferred forms of the present invention will now be described with reference to the accompanying drawings.

DETAILED DESCRIPTION OF THE PREFERRED EMBODIMENTS

The present invention provides a humidification chamber for use with a breathing assistance apparatus where the flow of gases to a user passes in sequence through a gases supply device or flow driver (a blower, fan or compressor unit), the humidification chamber, a heated delivery conduit and a patient interface, similar to that outlined in the prior art section above. The present invention also provides a breathing assistance apparatus that includes the humidification chamber.

The preferred form of the humidifier chamber of the present invention can be used with the system described above, in place of the chamber 5, or the chamber could be used with any other suitable breathing assistance apparatus.

The preferred form of the humidifier chamber will now be described with reference to FIGS. 2 to 5.

Figure 2A:
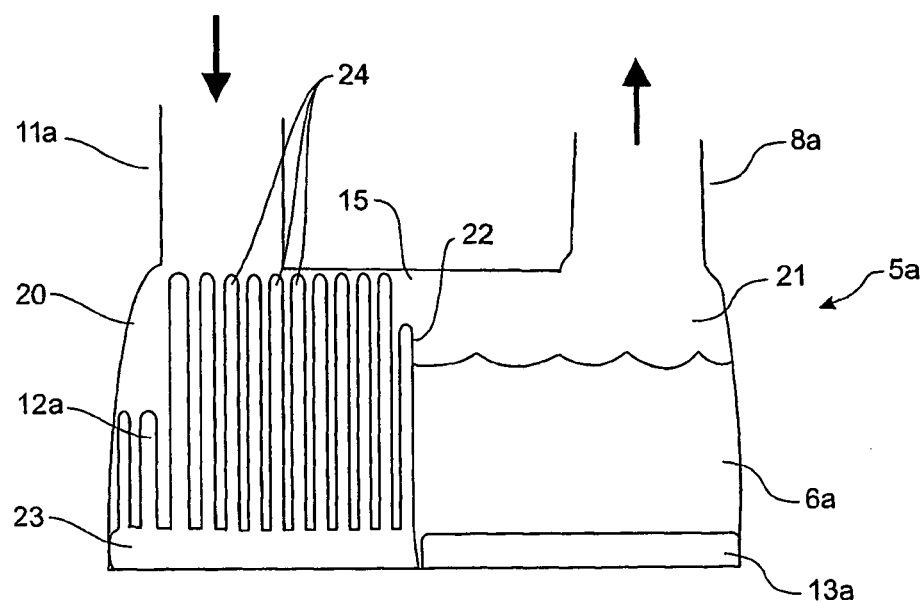
FIG. 2a shows a sectional side view of the humidifier chamber of the present invention that can be used with the breathing assistance apparatus of FIG. 1 in place of the prior art humidifier chamber, the humidifier chamber of the present invention having a fin heater occupying the upstream half of the chamber and forming a tortuous path through the chamber, and a separate heater base in the downstream half of the chamber.
Figure 2B:
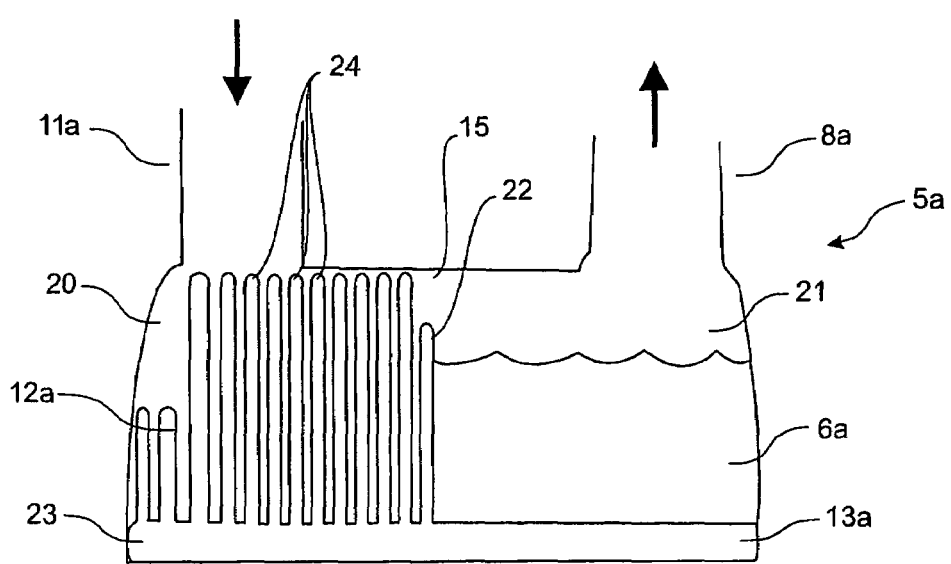
FIG. 2b shows the humidifier chamber of FIG. 2a, where the fin heater and the base are a single unit.
Figure 3:
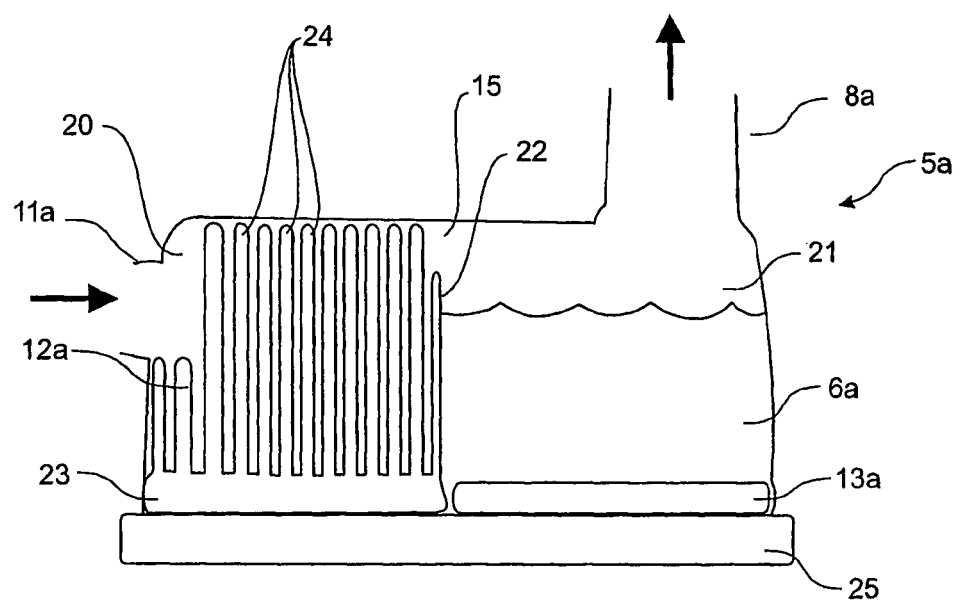
FIG. 3 shows a sectional side view of an alternative humidifier chamber layout that can be used with the breathing assistance apparatus of FIG. 1 in place of the prior art humidifier chamber, with the inlet located on the side wall of the chamber.
Figure 7:
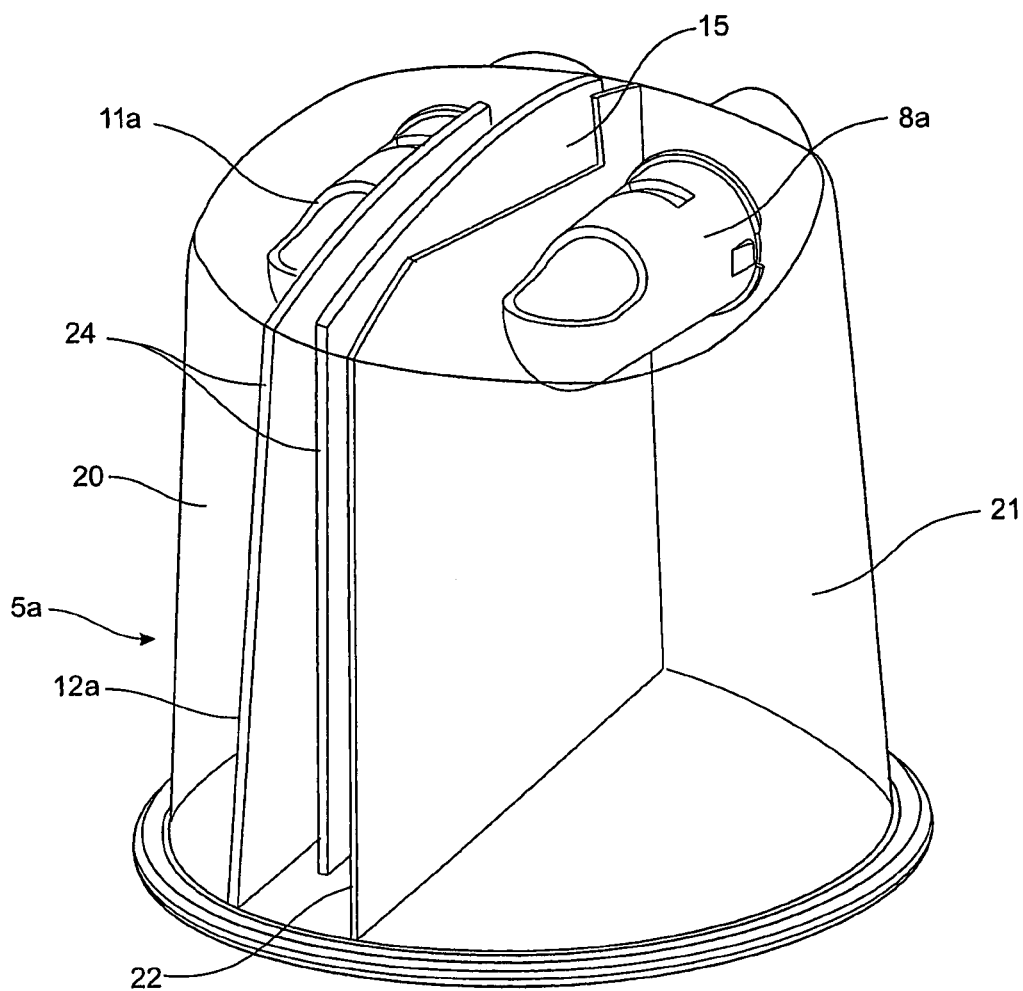
FIG. 7 shows a perspective view of an alternative humidifier chamber layout, with co-located inlet and outlet parts.

FIG. 2a shows a humidifier chamber 5a with an inlet port 11a and an outlet port 8a. The chamber 5a has a base 13a and in use is connected to a housing such as housing 10 so that a heater plate 25 on the housing 10 heats a volume of water 6a in the chamber 5a. In the embodiment shown in FIG. 2, chamber 5a has both the inlet 11a and outlet 8a located in the roof of the chamber. However, the present invention is not limited to this configuration, and the inlet and outlet ports 11a and 8a can be located wherever is convenient on the chamber 5a. For example, die inlet port can be located passing generally horizontally in through the side wall of the chamber 5a, as shown in FIG. 3. Alternatively, both the inlet and the outlet ports can be located next to each other, as shown in FIG. 7 in the side wall of the chamber. These configurations can be advantageous in certain circumstances. For example, they lend themselves more readily to a slide-on system. It should also be noted that in one of the embodiments shown, the base 13a is a separate unit from the finned heater 12a. This potentially allows the finned heater and the base 13a to be separately heated. However, as shown in FIG. 2b, the base 13a and the heater 12a can be single unit if required. This second configuration (single base) can be preferable if the chamber 5a is being used with an existing heater or base unit, as it allows both the heater 12a and the base 13a to be heated by the same heater plate 25. However, as noted above, the internal heater 12a and the base 13a can be separate items, heated separately in other configurations. For example, the chamber 5a can be used with a gases supply device that has a split heater plate, with each part of the split heater plate separately powered to separately heat the separate internal heater 12a and base 13a. Alternatively, one or both of the internal heater 12a and the base 13a could be configured as resistance heaters, connected to an electrical circuit or circuits to heat them either together, or separately.

Figure 5:
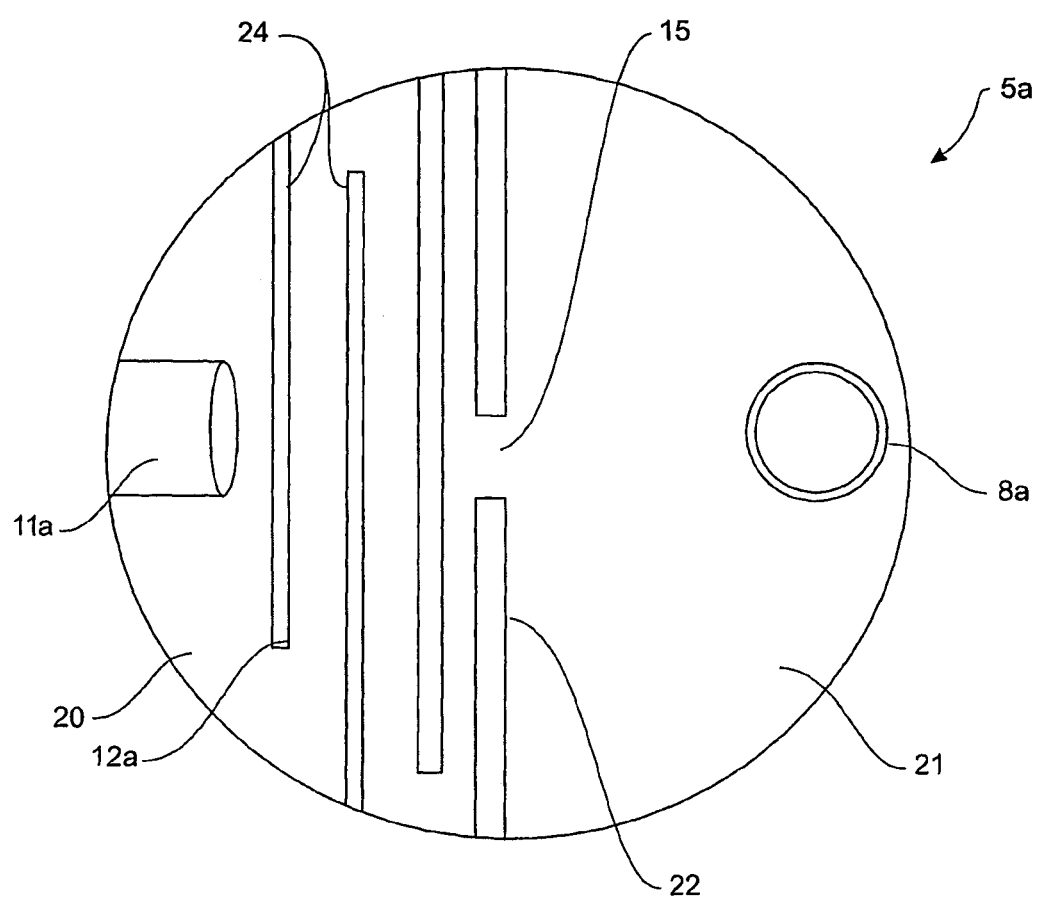
FIG. 5 shows a schematic plan view of the chamber of FIGS. 2 and 4, with one possible form of the tortuous path shown in the upstream part of the chamber.
Figure 6:
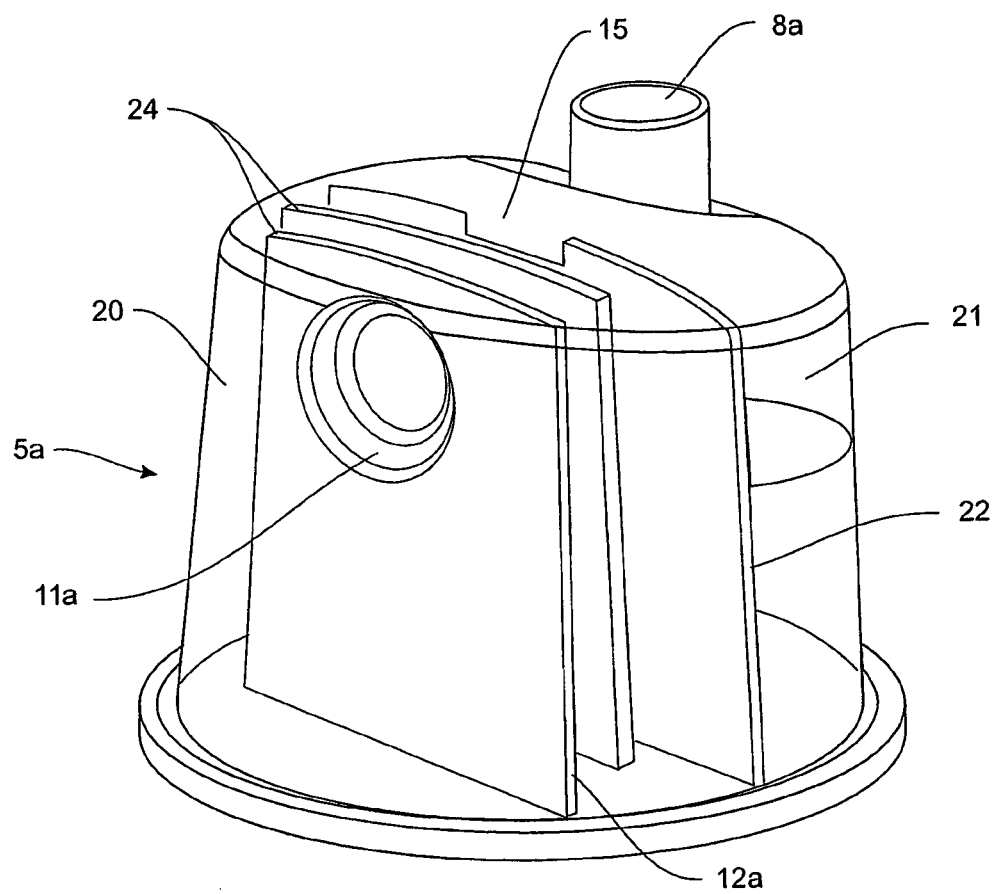
FIG. 6 shows a perspective view of the chamber of FIG. 5.

In the preferred embodiment, the chamber 5a is circular when viewed from above (plan view), as shown in FIG. 5. The chamber 5a is divided into two parts or halves, the two halves appearing semicircular when viewed from above. The two halves can be characterised as an 'upstream' half or upstream sub-chamber 20, and a 'downstream' half or downstream sub-chamber 21. In use, gas from the blower enters the upstream sub-chamber 20 via inlet port 11a, passes through the upstream sub-chamber 20 and the downstream sub-chamber 21, exiting the chamber 5a via outlet port 8a, which is located in the downstream half. The structure of the two sub-chambers 20, 21 of the preferred embodiment will now be described.

Figure 4:
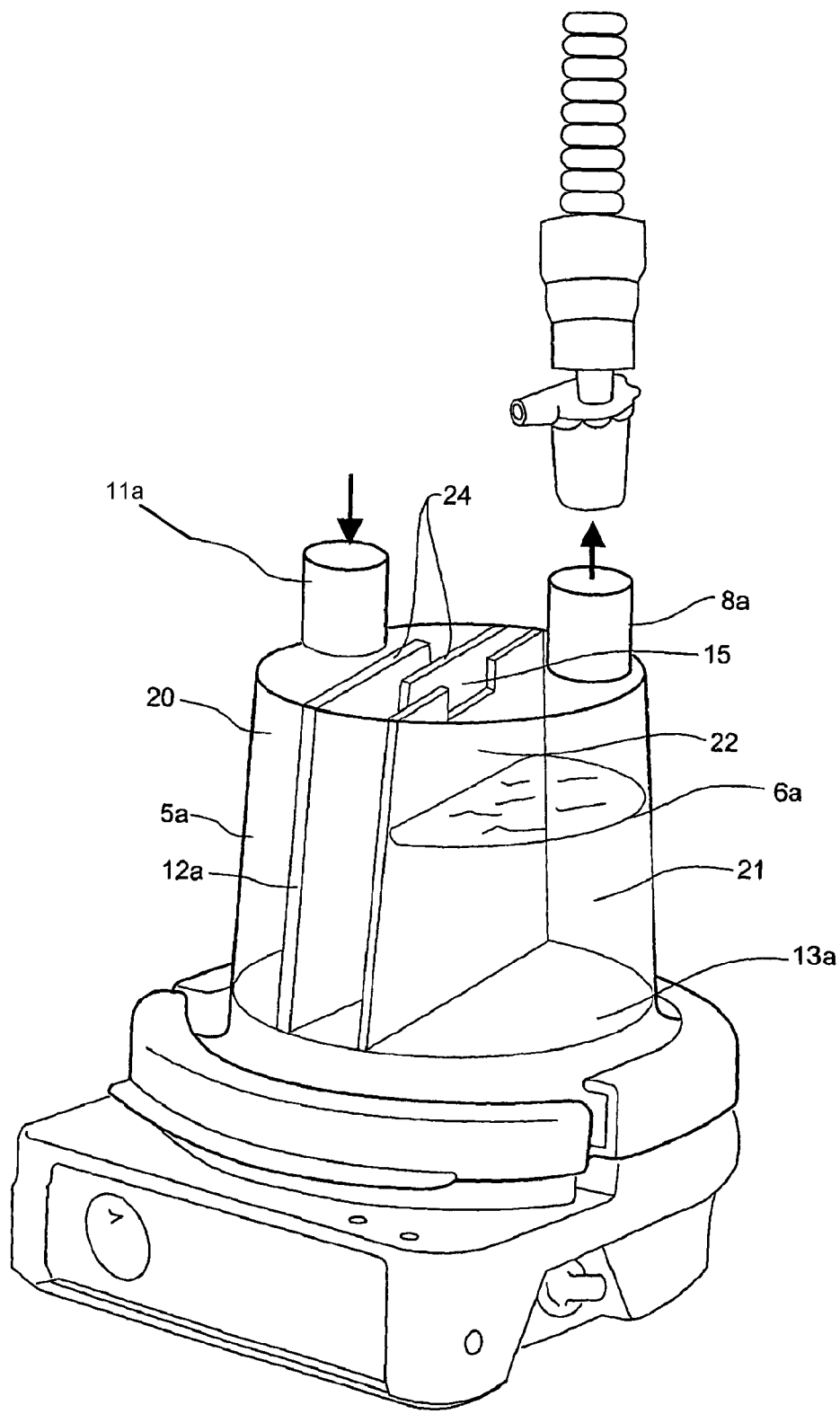
FIG. 4 shows a schematic perspective view of the chamber of FIG. 2, connected to a separate heater base unit and showing how the fins of the heater can form the tortuous path through the upstream half of the chamber.

Referring to FIGS. 3, 4 and 5, the downstream sub-chamber 21 is defined by the outer wall of the chamber 5a, a semi-circular heater base 13a, and a substantially vertical separating partition or wall 22 between the upstream and downstream sub-chambers. The wall 22 includes an aperture 15 that allows gases to pass from the upstream sub-chamber 20 into the downstream sub-chamber 21. In the preferred embodiment, the aperture 15 is located in the wall above the upper level of the water 6a, so that only gases can pass from the upstream sub-chamber 20 to the downstream chamber 21 in use. In use, the downstream sub-chamber 21 contains the volume of water 6a that is heated by the heater base 13a to humidify gases passing through the downstream sub-chamber 21. The aperture 15 is shown as a notch-shaped opening in the upper portion of the partition 22, but can be sized and positioned according to a users requirements. For example, the aperture could run the full width of the humidifier chamber if required, and be formed by making the partition 22 the same width as the chamber, but having less height than the chamber, so that when in position, there is a gap between the internal upper surface and the upper portion of the sides of the chamber, and the top edge of the partition, this gap defining the aperture 15. Alternatively, the partition or wall 22 could fit exactly in the chamber, but have an aperture machined through it, of a suitable size and at a suitable location.

The upstream sub-chamber 20 is defined by the separating wall 22, the wall of the chamber 5a, and a semicircular base 23. The upstream sub-chamber 20 contains an internal heater or finned heater 12a, which in the preferred embodiment is formed as one item with the base 23. The heater 12a is located in the chamber 5a so that part of the heater is immediately adjacent the inlet port 11a, so that gases entering the chamber immediately contact the heater 12a. The preferred embodiment of the heater 12a is configured and shaped so that gases entering the chamber must pass over, between, and around the fins 24. That is, the fins 24 act as a tortuous path that runs between the inlet 11a and the downstream sub-chamber 21. This ensures that gases passing through the upstream half of the chamber 5a have maximum exposure to the fins 24 of the heater 12a and substantially the entire volume of gases passing into the chamber 5a becomes heated. The preferred embodiment of the heater 12a is a series of parallel vertical fins 24 aligned perpendicular to the shortest or most direct path between the inlet 11a and the outlet 8a or aperture 15. However, in other embodiments the fins may have other orientations, such as horizontal depending on the location of the inlet to the chamber. In the preferred embodiment, each of the fins 24 is offset from adjacent or neighbouring fins to create a series of spaces on alternating sides of the fins 24, these spaces forming a path for the gases between the inlet 11a and the aperture 15. This arrangement is shown schematically in FIGS. 4 and 5. In order to increase efficiency, the fins 24 are sized and shaped so that they contact the wall and roof of the chamber 5a, except for the side spaces. This ensures that the majority of the gases will pass along the tortuous path, and will not follow a direct route between inlet and aperture. If required, the contact between fins and wall can be reinforced by using a sealant or such as silicone or similar. Alternatively, die spaces can be formed both on alternating sides and also at the top and at the base of the fins 24. The tortuous path ensures that there is no direct path that the gases can take between the inlet 11a and the aperture 15, and ensures that substantially the entire volume of gases passing through the upstream sub-chamber 20 is heated to an optimal temperature.

The upstream sub-chamber 20 is separated from the downstream sub-chamber 21 by the partition or wall 22, which in the preferred embodiment is an integral part of the heater 12a, and forms a final fin of the heater 12a. It should be noted that the partition wall 22 could be a separate item to the heater 12a if required. The final fin or wall 22 is sealed to the sides and base of the chamber 5a, ensuring that the volume of water in the downstream sub-chamber 21 remains in the downstream half of the chamber 5a, and has no contact with the heater 12a (except for the wall or final fin 22). Therefore, the gases remain dry as they pass through the upstream sub-chamber 20.

It should be noted that the spacing between the fins 24 in the preferred embodiment is such that the gases can pass freely over and around the fins 24 without the system requiring significant additional pressure from the blower to force the gases through the chamber 5a. The aperture 15 is also sized so that it does not create a bottleneck or cause back pressure in the system.

The heated gases enter the downstream half of the chamber 5a via the aperture 15 in the wall 22. As outlined above, the downstream sub-chamber 21 contains a volume of water 6a, which is heated by contact with the heater base 13a. As the heated gases pass through the space above the volume of water 6a, they become humidified. The heated humidified gases then pass out of the humidifier chamber 5a via the outlet port 8a into a delivery conduit, such as delivery conduit 3 previously described. It is preferred that the chamber 5a is used with a heated delivery conduit, so as to prevent the water vapour in the heated humidified gases from condensing.

In the preferred embodiment, and as described above, the heater base 13a is separate heater from the finned heater 12a, with the two units connected to form a sealed base for the chamber 5a. Keeping the heaters 12a and 13a as separate units has the advantage as they can be independently controlled. However, if required, the heater 12a and the heater base 13a can be manufactured as a single item, allowing it to be powered and controlled from a single power source.

By heating the gases within the chamber immediately before they contact the humidified water vapour in the downstream sub-chamber 21, the gases are heated to an optimum temperature. This allows them to become fully saturated when they contact the water vapour. The gases do not have an opportunity to cool before exposure to the water vapour.

By using a tortuous path when heating the gases, substantially the whole of the gas volume becomes heated. The tortuous path layout makes it difficult for the gases to form an insulating cushion, e.g. next to a heated conduit wall, which can occur in linear flow due to gases shearing effects. This gases shearing effect allows die greater part of the gas volume to pass through the heated area without being heated to the required temperature.

Preheating the air immediately prior to humidification also ensures that the humidified gases exiting the chamber via outlet 8a remains at the optimum required temperature. This helps ensure that the gases are delivered to the patient at the required temperature.

Figure 1:
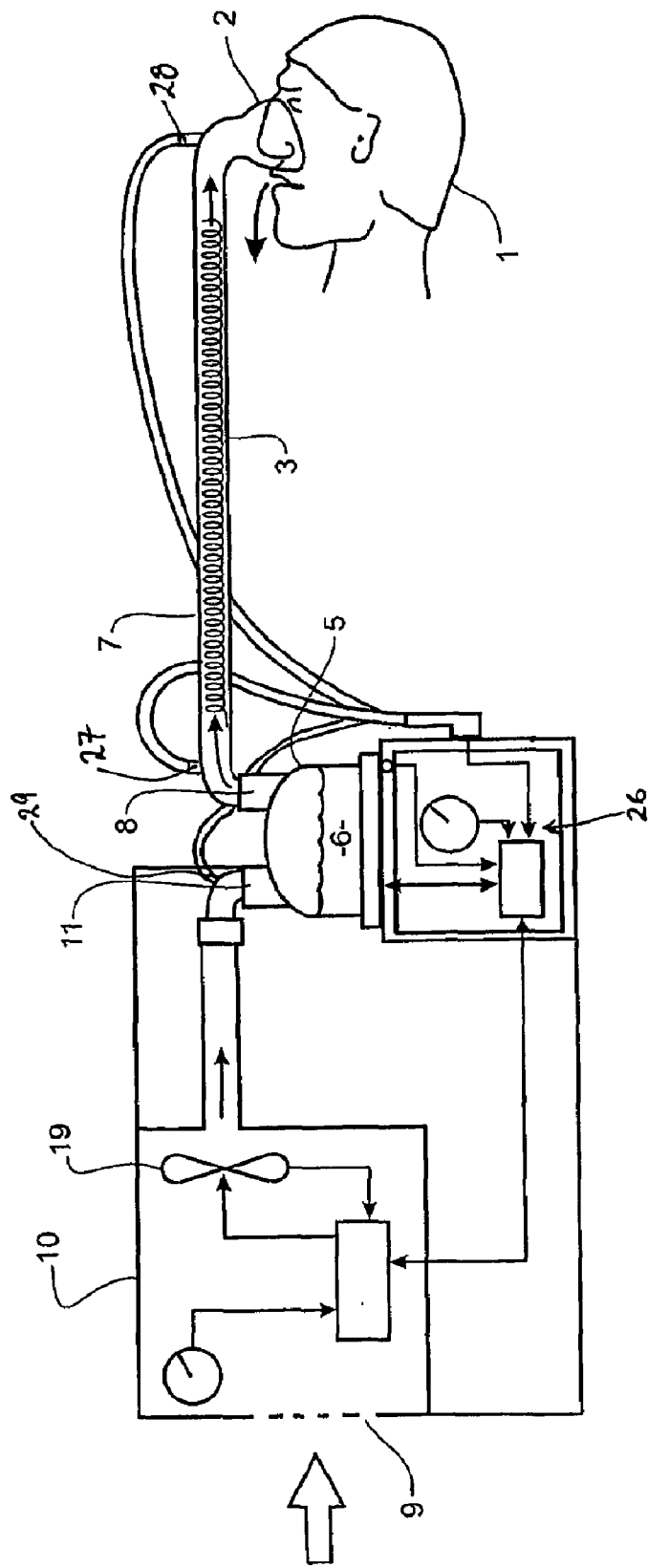
FIG. 1 shows a schematic view of a prior art breathing assistance apparatus for delivery of heated and humidified gases to a user or patient, the apparatus including a humidifier chamber.

The heater plate or heater plates (as described above) are controlled by a control unit (generally indicated as 26 in FIG. 1) in the humidification unit. The control unit is generally a microcontroller, which is connected to at least one sensor, and can potentially be connected to a number of sensors. For example, a chamber exit sensor 27 may be provided, or a patient sensor 28 which is located at the patient end of tube/conduit 7 or located on or in the interface 2. Alternatively, both a chamber exit sensor 27 and a patient end sensor 28 may be provided. A chamber inlet sensor 29 could also be provided. Any combination of these sensors 27, 28, 29 could also be provided, each one connected to the control unit 26. It should be noted that the three locations specified above are the preferred locations. However, other locations for the sensors can be used as necessary. For example, it might be advantageous to measure the temperature or humidity at the aperture 15.

The sensor or sensors measure parameters at their location. The data from the sensor or sensors is fed back into the control unit, so that heater plate temperatures can be controlled and constantly changed in a real time manner to provide predetermined or maximum temperature or humidity of the gases at these various points in the whole system. Therefore, any or all of the sensors 27, 28 and 29 may be either or both of temperature sensors or humidity sensors (either absolute humidity or relative humidity sensors).

Tests were conducted to determine whether a humidification chamber with internal heating of the present invention would provide a higher absolute humidity to patients compared to a standard chamber. The humidification chamber with internal heating ("heating chamber") used in the test was of the type described in FIG. 2b. A standard chamber such as the Fisher & Paykel Healthcare Limited HC345 chamber was used.

Figure 8:
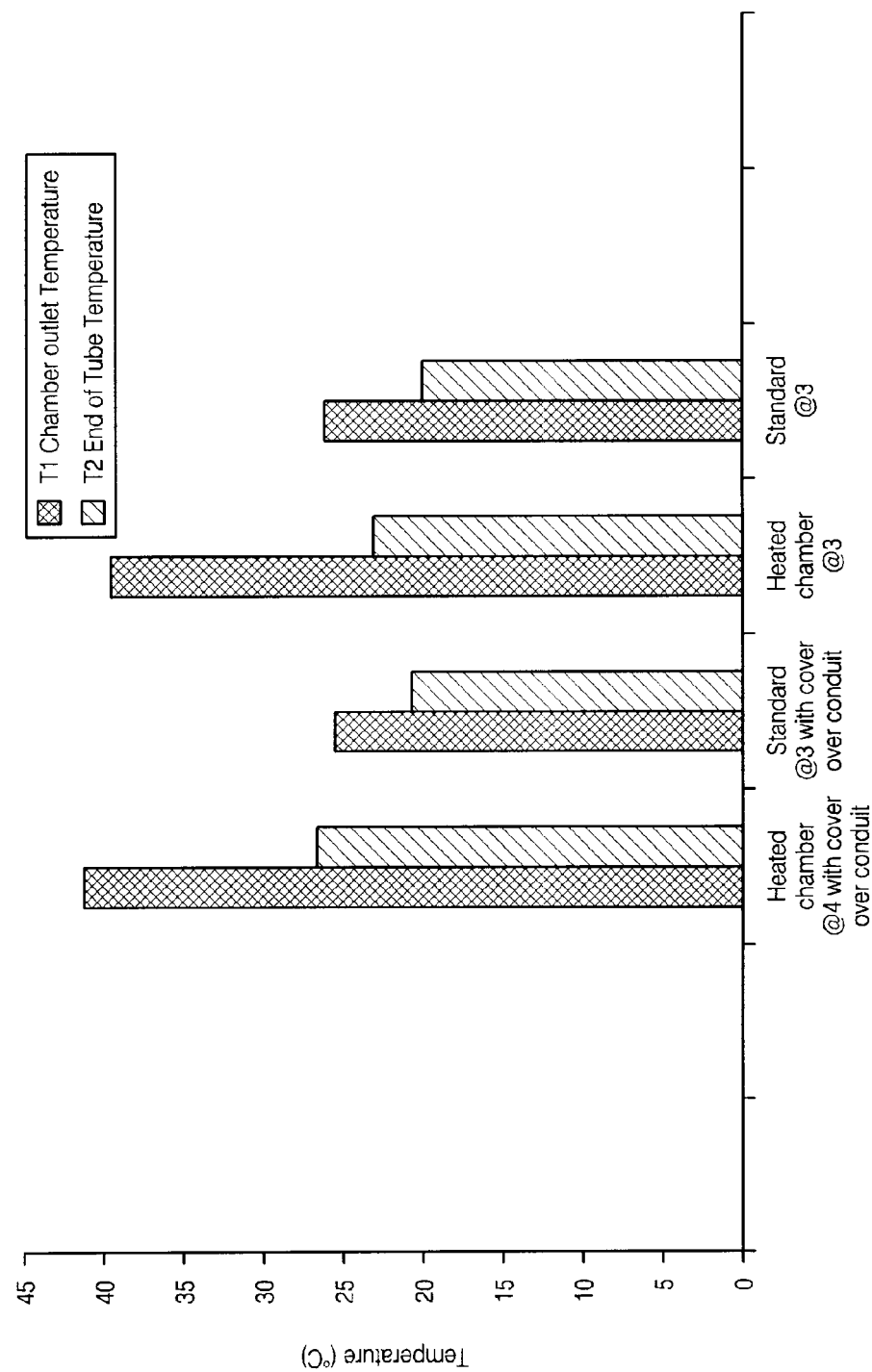
FIGS. 8-10 show test results allowing a comparison of chamber exit temperatures between heated chambers and standard chambers.
Figure 9:
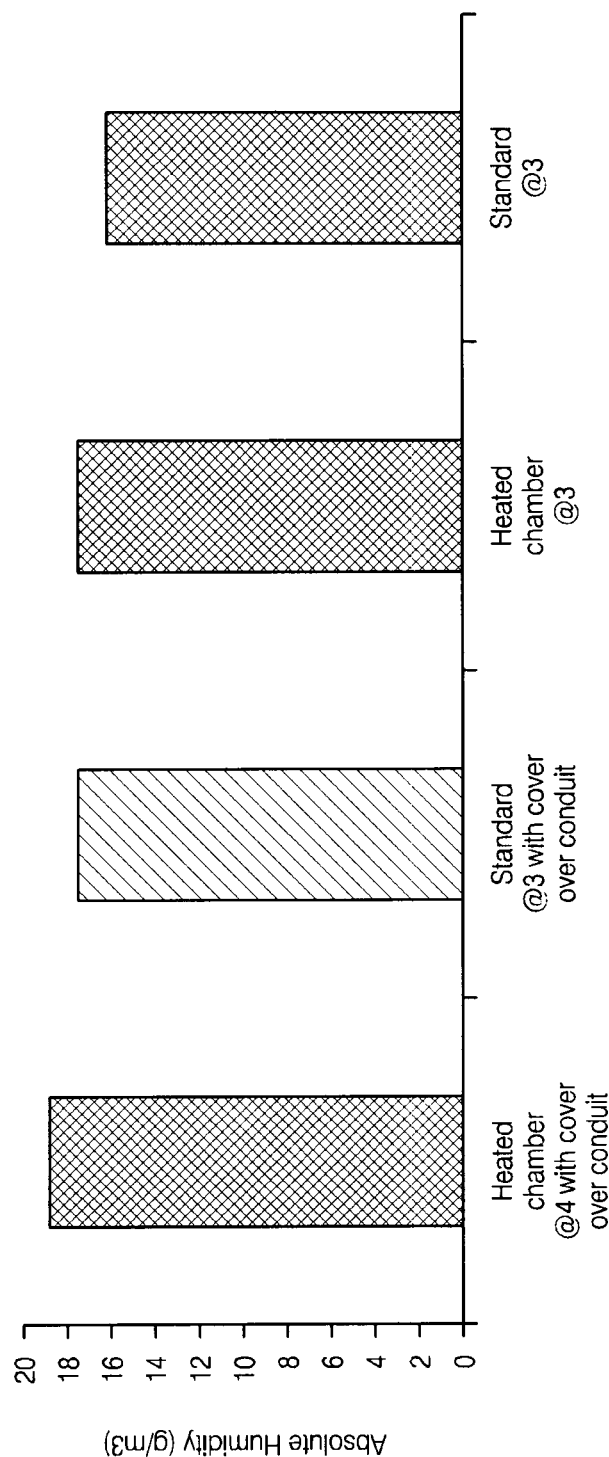
Figure 10:
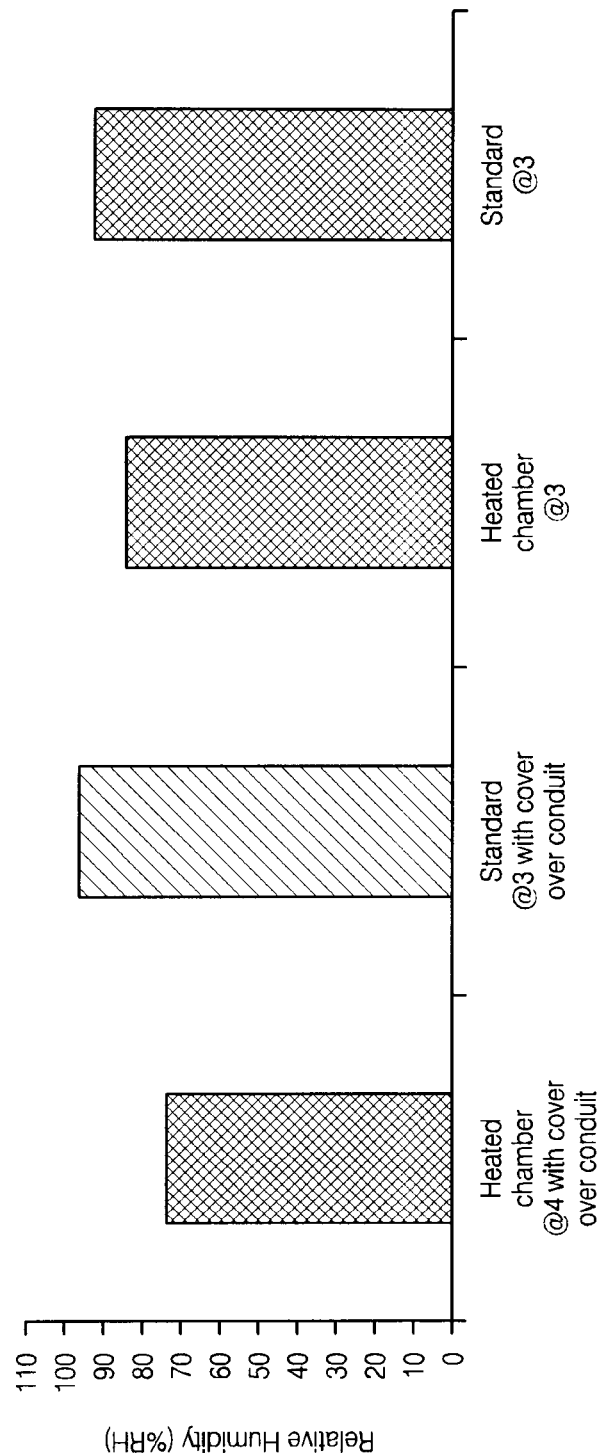

Test results are shown in FIGS. 8-10. These results indicate that the heated chamber of the present invention provided a higher chamber exit temperature compared to the standard chamber (FIG. 8). In general, the heated chamber provided an exit temperature of approximately 10° C. greater then the standard chamber at the same gases pressure and heater plate setting. Heater plate settings of either 3 or 4 were used. Each of these settings related to a particular controlled temperature of the heater plate. The end of tube temperature, that is, at the patient end 2 of the conduit 3, was higher for the heated chamber.

FIG. 9 shows absolute humidity outputs. The absolute humidity output of the heated chamber was about 10% above the standard chamber. FIG. 9 shows that the heated chamber allows the user of a higher heater plate setting (4 as opposed to 3) without the introduction of condensation in the conduit. Therefore, the absolute humidity of the gases supplied to the patient was higher for the heated chamber.

FIG. 10 shows relative humidity outputs at a maximum humidity setting without causing any rain out (condensation) in the conduit 3. The relative humidity for the standard chamber is higher than the heated chamber.

The invention claimed is:

1. A respiratory humidifier chamber for use with a breathing assistance apparatus, comprising:
a watertight vessel having an inlet adapted for receiving gases from said breathing assistance apparatus, and a separate outlet through which heated humidified gases exit said vessel for delivery to a patient, said vessel being removable from and attachable to said breathing assistance apparatus,
said vessel comprising a partition dividing said vessel into an upstream sub-chamber and a downstream sub-chamber, said sub-chambers being directly adjacent each other and being sealed from each other by said partition except for an aperture, said aperture passing through said partition and allowing gaseous communication between said sub-chambers,
said downstream sub-chamber having a heater base adapted to heat a volume of water contained within said downstream sub-chamber in use, said aperture, said inlet and said outlet located above said volume of water in use,
said upstream sub-chamber containing an internal heater adapted to heat gases passing through said upstream sub-chamber from said inlet to said aperture, at least part of said internal heater located immediately adjacent said aperture.

2. A respiratory humidifier chamber as claimed in claim 1 wherein said internal heater is configured so as to provide a tortuous path for said gases as they pass through said upstream sub-chamber.

3. A respiratory humidifier chamber as claimed in claim 2 wherein said internal heater is a fin heater having a plurality of fins.

4. A respiratory humidifier chamber as claimed in claim 3 wherein the fins of said fin heater are aligned substantially perpendicular to a direct flow path between said inlet and said aperture.

5. A respiratory humidifier chamber as claimed in claim 3 wherein said tortuous path is formed by offsetting adjacent ones of said fins.

6. A respiratory humidifier chamber as claimed in claim 1 wherein said heater base and said internal heater are separate.

7. A respiratory humidifier chamber as claimed in claim 6 wherein said chamber also has at least one sensor adapted to provide data to a remotely located controller.

8. A respiratory humidifier chamber as claimed in claim 7 wherein said chamber also has at least one a sensor located at said outlet.

9. A respiratory humidifier chamber as claimed in claim 7 wherein said chamber also has at least one a sensor located at said inlet.

10. A respiratory humidifier chamber as claimed in claim 7 wherein said at least one sensor is located at said inlet and said chamber has a second sensor located at said outlet.

11. A respiratory humidifier chamber as claimed in any one of claims 8 to 10 wherein said sensors are either temperature sensors or humidity sensors, or both.

12. A respiratory humidifier chamber as claimed in claim 11 wherein said sensors are at least humidity sensors adapted to sense either relative or absolute humidity.

13. A respiratory humidifier chamber as claimed in claim 1 wherein said heater base and said internal heater are formed as a single heater, adapted to be heated from a single source.

14. A respiratory humidifier chamber as claimed in claim 13 wherein said chamber also has at least one sensor adapted to provide data to a remotely located controller.

15. A respiratory humidifier chamber as claimed in claim 14 wherein said chamber also has at least one sensor located at said outlet.

16. A respiratory humidifier chamber as claimed in claim 14 wherein said chamber also has at least one sensor located at said inlet.

17. A respiratory humidifier chamber as claimed in claim 14, wherein said at least one sensor is located at said inlet and said chamber has a second sensor located at said outlet.

18. A respiratory humidifier chamber as claimed in claim any one of claims 15 to 17 wherein said sensors are either temperature sensors or humidity sensors, or both.

19. A respiratory humidifier chamber as claimed in claim 18 wherein said sensors are at least humidity sensors adapted to sense either relative or absolute humidity.

20. A breathing assistance apparatus for delivery of respiratory gases to a patient comprising:
a gases supply device adapted to provide a flow of pressurised gases through said system apparatus,
a humidifier chamber having an inlet and a separate outlet, said chamber adapted to receive said flow of gases from said breathing assistance apparatus via said inlet and provide a supply of heated humidified gases through said outlet, a delivery conduit adapted to connect to said outlet and receive said heated humidified gases, a patient delivery interface adapted to receive said gases from said delivery conduit and deliver said gases to said patient, said humidifier chamber comprising a watertight vessel, said watertight vessel being removable from and attachable to said breathing assistance apparatus, said watertight vessel having a partition dividing said vessel into an upstream sub-chamber and a downstream sub-chamber, said sub-chambers being directly adjacent each other and being sealed from each other except for an aperture passing through said partition, said aperture allowing gaseous communication between said sub-chambers, said downstream sub-chamber having a heater base adapted to heat a volume of water contained within said downstream sub-chamber in use, said aperture, said inlet and said outlet located above said volume of water in use, said upstream sub-chamber containing an internal heater adapted to heat gases passing through said upstream sub-chamber from said inlet to said aperture, at least part of said internal heater located immediately adjacent said aperture.

21. A breathing assistance apparatus as claimed in claim 20 wherein said breathing assistance apparatus also has a heater plate adapted to heat said heater base and said internal heater.

22. A breathing assistance apparatus as claimed in claim 21 wherein said heater plate is a single heat source and heats said heater base and said internal heater together.

23. A breathing assistance apparatus as claimed in claim 21 wherein said heater plate is adapted to heat said heater base and said internal heater separately.

24. A breathing assistance apparatus as claimed in any one of claims 21 to 23 wherein said breathing assistance apparatus also has at least one outlet sensor located at or close to said chamber outlet, said outlet sensor adapted to provide data to a remotely located controller, and a controller adapted to receive data from at least said outlet sensor and control and change the temperature of said heater plate.

25. A respiratory humidifier chamber as claimed in claim 24 wherein said outlet sensor is either a temperature sensor or a humidity sensor, or both.

26. A breathing assistance apparatus as claimed in any one of claims 21 to 23 wherein said breathing assistance apparatus also has at least one inlet sensor located at or close to said chamber inlet, said inlet sensor adapted to provide data to a remotely located controller, and a controller adapted to receive data from at least said inlet sensor and control and change the temperature of said heater plate.

27. A respiratory humidifier chamber as claimed in claim 26 wherein said outlet sensor is either a temperature sensor or a humidity sensor, or both.

28. A breathing assistance apparatus as claimed in any one of claims 21 to 23 wherein said breathing assistance apparatus also has a first sensor located at or close to said inlet and a second sensor located at or close to said outlet, and a controller adapted to receive data from at least said first and second sensors and control and change the temperature of said heater plate.

29. A respiratory humidifier chamber as claimed in claim 28 wherein said outlet sensor is either a temperature sensor or a humidity sensor, or both.

* * * * *